United States Patent [19]

Javdani et al.

[11] Patent Number: 4,482,751

[45] Date of Patent: Nov. 13, 1984

[54] METHOD FOR PREPARATION OF 8-METHOXY-4,8-DIMETHYL-1-(4-ISO-PROPYLPHENYL)-NONANE

[75] Inventors: Kambiz Javdani, Walnut Creek; William J. Welch, Benicia, both of Calif.

[73] Assignee: Stauffer Chemical Company, Westport, Conn.

[21] Appl. No.: 465,943

[22] Filed: Feb. 14, 1983

[51] Int. Cl.$^3$ .............................................. C07C 41/18
[52] U.S. Cl. ....................................... 568/626; 568/9
[58] Field of Search ................................... 568/626, 9

[56] References Cited

U.S. PATENT DOCUMENTS 4,002,769  1/1977  Schwarz et al. ................ 568/626 X

OTHER PUBLICATIONS

Adams et al., Organic Reactions, vol. 14, (1965), 388–389.

*Primary Examiner*—Bernard Helfin
*Attorney, Agent, or Firm*—Paul R. Martin

[57] ABSTRACT

Disclosed is a method for the preparation of 8-methoxy-4,8-dimethyl-1-(4-isopropylphenyl)-nonane which comprises the steps of (a) reacting para-isopropylbenzyl chloride with triphenylphosphine in the presence of a suitable solvent for a sufficient period of time and at a sufficient temperature to form an intermediate product in solution, para-isopropylbenzyl triphenylphosphonium chloride, and (b) reacting said solution with sodium methoxide, followed by methoxycitronellal to produce cis- and trans-8-methoxy-4,8-dimethyl-1-(4-isopropylphenyl)-1-nonene, (c) separating said intermediate product from the residual reactants, and (d) hydrogenating said cis- and trans-8-methoxy-4,8-1-(4-isopropylphenyl)-1-nonene, in the presence of a suitable solvent and catalyst to form 8-methoxy-4,8-dimethyl-1-(4-isopropylphenyl)-nonane.

13 Claims, No Drawings

METHOD FOR PREPARATION OF 8-METHOXY-4,8-DIMETHYL-1-(4-ISOPROPYL-PHENYL)-NONANE

BACKGROUND OF THE INVENTION

This invention relates to a process for the preparation of 8-methoxy-4,8-dimethyl-1-(4-isopropylphenyl)-nonane, a compound which is used as an insecticide for the purpose of controlling fire ants.

Fire ants are a nuisance to farmers, particularly in the Southern states, because they build mounds in fields, which makes it difficult to cultivate crops. In addition, machinery or equipment passing over the mounds is subject to damage. They also attack livestock and people in the field which they come into contact with. Fire ants are so named because when they bite there is a painful fire-like sting associated with the bite.

The compound 8-methoxy-4,8-dimethyl-1-(4-isopropylphenyl)nonane is patented by the U.S. Government under U.S. Pat. No. 4,002,769 and is disclosed to be useful in the control of flies and mosquitoes. As disclosed in the patent, this compound has been made by reacting para-isopropylbenzyl chloride with triphenylphosphine in the presence of an acetonitrile solvent to form paraisopropylbenzyl triphenylphosphonium chloride. The latter compound is in turn reacted with sodium methoxide followed by methoxycitronellal to produce the intermediate cis- and trans-8-methoxy-4,8-dimethyl-1-(4-isopropylphenyl)1-nonene, and this compound, in turn, is hydrogenated to form the end product.

The intermediate compound, sometimes referred to herein as dehydro MV-678, has the formula

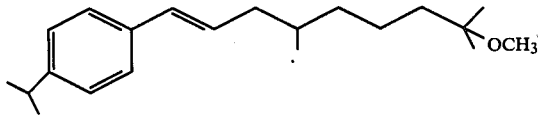

The end product, sometimes referred to as MV-678, has the formula

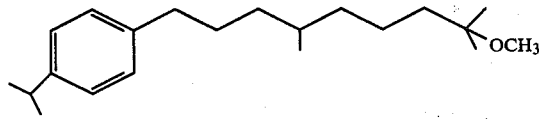

Toluene has also been used as a solvent in the process for the production of the intermediate.

A specific problem which occurs in the process for making 8-methoxy-4,8-dimethyl-1-(4-ispropylphenyl)-nonane lies in the fact that at the end of the step involving the reaction of para-ispropylbenzyl chloride with triphenylphosphine, a solid is formed in the solution, that solid being para-isopropylbenzyl triphenylphosphonium chloride, and this solid is difficult and expensive to treat because it must be isolated and purified from the reactants, before the next step of the process.

This invention is thus concerned with a new and more economical process for the preparation of 8-methoxy-4,8-dimethyl-1-(4-isopropylphenyl)-nonane wherein the solid intermediate remains in solution or in a slurry without the need for isolation and purification, and the entire reaction is conducted in a liquid medium until such time as the end product is formed.

BRIEF DESCRIPTION OF THE INVENTION

It has now been discovered that 8-methoxy-4,8-dimethyl-1-(4-isopropylphenyl)-nonane can be prepared by a process which comprises:

(a) reacting para-isopropylbenzyl chloride with triphenylphosphine in the presence of an organic solvent selected from unsaturated or saturated alcohols having from 1 to 10 carbon atoms, to form para-isopropylbenzyl triphenylphosphonium chloride in solution in said solvent, (b) reacting said para-isopropylbenzyl triphenylphosphonium chloride in solvent solution with first sodium methoxide and then methoxycitronellal to produce in solution cis- and trans-8-methoxy-4,8-dimethyl-1-(4-isopropylphenyl)-1-nonene, (c) extracting said 8-methoxy-4,8-dimethyl-1-(4-isopropylphenyl)-1-nonene from the solvent solution, and (d) hydrogenating said cis- and trans-8-methoxy-4,8-dimethyl-1-(4-isopropylphenyl)-1-nonene, in the presence of a suitable solvent and catalyst to form the insecticide, 8-methoxy-4,8-dimethyl-1-(4-isopropylphenyl)-nonane.

The preferred solvent for use in step (a) above is methanol. It has been fournd that when the preferred methanol is used as a solvent the product not only remains in solution, but the reaction itself is approximately ten times faster than the process in accordance with the previous method which utilized toluene as a solvent. Other suitable solvents which can be used include other alcohols and polar solvents such as ethanol, propanol, isopropanol and the like.

Preferably, for every 0.25 gram moles of active ingredient used, 200 milliliters of methanol are added as a solvent. The amount of methanol which can be used is variable. However, the lower limit would be that amount in which the product para-isopropylbenzyl triphenylphosphonium chloride becomes saturated in the methanol and starts to crystallize out.

When para-isopropylbenzyl chloride is reacted with the triphenylphosphine in n-octane as a solvent, the reaction is normally completed after 25–30 hours and the product precipitates as a solid and forms a slurry solution. The slurry is then washed with methanol in order to dissolve the phosphonium chloride salt. After phase separation, the phosphonium chloride salt is thus removed from the n-octane solvent and incorporated into the methanol solvent. Thus, a critical feature of the first step of the invention when a solvent other than methanol is used first is that the second solvent used, such as methanol, must be sufficiently immiscible in the first solvent so as to effect a phase separation, but at the same time the solvent must be capable of dissolving the product formed.

Step (a) of the process set forth above is normally completed within about 4–5 hours when methanol is used as the solvent and 25–30 hours when n-octane is used, although the time for carrying out the reaction will be variable, depending on other process conditions and yield requirements.

The entire reaction is preferably conducted at atmospheric pressure, and when it is conducted at atmospheric pressure, the reactants in step (a) are desirably heated to just the boiling point of the solvent, which in the case of methanol is approximately 65°–67° C.

The reaction can be conducted with pressure, and in that instance, somewhat higher temperatures can be used. It is preferred, however, that the reaction is conducted in atmospheric pressure.

The intermediate product formed in step (b) is separated from the residual reactants by adding hydrogen peroxide which converts the remaining triphenylphosphine to triphenylphosphine oxide. Hexane or other suitable solvent is then added to extract the dehydro intermediate. After washing the extract with methanol and water to remove triphenylphosphine oxide, the hexane is then stripped off.

After the stripping, the cis- and trans-8-methoxy-4,8-dimethyl-1-(4-isopropylphenyl)-1-nonene is converted to the specific insecticide for fire ants by hydrogenating the intermediate product in the presence of a suitable solvent, such as ethanol, methanol, isopropanol, or hexane, and a suitable catalyst, usually 5% palladium on carbon. After this reaction is complete, the catalyst is recovered and the solution is stripped to remove the solvent, yielding the end product.

This invention will be more clearly understood with reference to the following examples, which are intended to be illustrative only of the invention, but not limiting thereof.

EXAMPLE 1

A suitable round-bottom flask was obtained and to this flask was charged 65.5 grams (g) (0.25 mole) of triphenylphosphine, 42.3 g (0.25 mole) of para-isopropylbenzyl chloride, and 210 ml of methyl alcohol. The reaction mixture was heated to reflux and refluxed for approximately 5 hours. At the end of that time, the heat was turned off and the product isolated, yielding 252.1 g of the solution of para-isopropylbenzyl triphenylphosphonium chloride in methanol.

249.1 g (0.231 mole of para-isopropyl triphenylphosphonium chloride) of the latter compound was charged into a second reaction vessel along with 49.68 g (0.23 mole of sodium methoxide) of a 25% solution of sodium methoxide in methanol at 10° C. and 34.22 g (0.184 mole) of methoxycitronellal. The reaction vessel was initially surrounded by an ice bath and the ice bath was subsequently removed and the reactants allowed to warm to room temperature. After three hours the reaction was subsequently heated to reflux, and refluxing was continued for approximately one hour.

Thereafter, the heat was turned off, and the reaction solution allowed to cool to 30° C. Next, 8 g of a 30% solution of hydrogen peroxide was charged to the reaction solution, and the contents were allowed to agitate for 45 minutes. Next, 100 ml of water and 250 ml of hexane were added and agitation was continued for an additional 15 minutes. The contents were then allowed to set and achieve phase separation. The phases separated into an aqueous and organic phase. The organic phase was washed with 30 g of water and 75 g of methyl alcohol, and the phases were again allowed to separate. Next, the organic phase was stripped at approximately 100° C. under full vacuum and a nitrogen purge for one hour. Approximately 50 g of the intermediate product, 8-methoxy-4,8-dimethyl-1-(4-isopropylphenyl)-1-nonene, was obtained.

Next, 12.5 g of the product was mixed with 1.9 g of hexane in the presence of 0.6 g of a palladium carbon catalyst and reacted with hydrogen under 50 psia pressure. The solution was thereafter filtered, and washed with 250 ml of hexane and again stripped under full vacuum at 90° C. with a nitrogen purge. The product recovered, was the desired end product, 8-methoxy-4,8-dimethyl-1-(4-isopropylphenyl)-nonane.

EXAMPLE 2

A one liter reactor was obtained, and to this reactor was charged 78.6 g (0.3 mole) of triphenylphosphine, 250 ml of methyl alcohol, and 50.7 g of para-isopropylbenzyl chloride. The solution was heated to reflux temperature and maintained at reflux for 5 hours. 327.3 g of a 40% solution of para-isopropylbenzyltriphenylphosphonium chloride in methanol was obtained, and to this was added 68.4 g of a 25% solution of sodium methoxide at 10° C., plus 46.5 g of methoxycitronellal also at 10° C. The reactants were allowed to agitate at room temperature approximately 3 hours and thereafter heated to reflux and maintained at reflux for one hour. The reactants were then cooled to room temperature, then charged with 4.5 g of 30% hydrogen peroxide solution and agitated for ½ hour. Thereafter the reaction solution was charged with 250 ml of hexane and 100 ml of water and agitated for an additional ½ hour. The reaction mixture was allowed to phase separate, and the aqueous phase was decanted off. The organic phase was then charged with 70 ml of methyl alcohol and 30 ml of water and again agitated for ½ hour. The aqueous phase was again decanted. The organic phase was then stripped at 110° C., under a full vacuum and nitrogen purge for 2 hours. There was obtained 63.5 g of the intermediate product, 8-methoxy-4,8-dimethyl-1-(4-isopropylphenyl)-1-nonene.

Thereafter, 50.8 g of this product was hydrogenated by reaction with 1.2 g of 50% water wet 5% palladium on carbon catalyst and 10 g of ethyl alcohol. The solution was filtered and washed with ethyl alcohol and stripped at 100° C. under full vacuum with a nitrogen purge for one hour. The residual product was analyzed by suitable techniques, and found to be the desired 8-methoxy-4,8-dimethyl-1-(isopropylphenyl)nonane.

EXAMPLE 3

A 5 liter reactor was obtained, and to this reactor was charged 655 g of triphenylphosphine, 1050 ml of methyl alcohol, and 422.5 g of para-isopropylbenzyl chloride. The reactants were heated to reflux temperature, approximately 65°-67° C., and refluxed for about 5 hours. There was obtained 1856.9 g of a 50% solution of para-isopropylbenzyl triphenylphosphonium chloride in methyl alcohol.

Thereafter, 1852 g of 50% para-isopropylbenzyl triphenylphosphoniium chloride in methyl alcohol was charged into the reaction vessel along with 464.4 g of a 25% solution of sodium methoxide in methanol and 332.9 g of methoxycitronellal. The reactants were charged at about 10° C. which was maintained by an ice bath. The ice bath was removed after the charging was completed.

The reactants were allowed to react at ambient temperature for about 3 hours and subsequently heated to reflux temperature at about 65° C. and refluxing was continued for approximately one hour.

Thereafter, the heat was removed and the reaction solution was charged with 45 g of a 30% hydrogen peroxide solution, and agitated for 30 minutes. Next, 1000 ml of water and 1500 hexane were charged, and the reactants again agitated for 30 minutes.

The contents were then allowed to separate over a period of approximately one-half hour. The aqueous phase contained approximately 3110 ml of material and the organic phase 2110 ml. The organic phase was then washed with 960 ml of methyl alcohol and 300 ml of water, and agitated for approximately one-half hour.

The phases were then allowed to separate, yielding 1532.6 g (1480 ml) of organic phase. The organic phase was then stripped at 100° C. under full vacuum with a nitrogen purge for one hour. There was obtained 555.4 g of dehydro-MV-678. This material was further stripped at 100° C. under a full vacuum with a nitrogen purge for an additional hour. Thereafter there was added 250 ml of hexane plus 250 ml of dehydro-MV-678, and the contents were stripped at 100° C. under full vacuum with a nitrogen purge for a period of two hours. The product obtained was 8-methoxy-4,8-dimethyl-1-(4-isopropylphenyl)-1-nonene.

EXAMPLE 4

A large round-bottom flask was obtained and into this flask was charged 150 ml (102.4 g) n-octane having 99% purity, 84.6 g para-isopropylbenzyl chloride and 111.5 g triphenylphosphine. The reaction solution was heated to 95°–100° C. and maintained at that temperature for approximately 29 hours. At that time the heat was turned off and the reaction solution was cooled and charged with 197.5 methyl alcohol to dissolve the suspended solids. The methanol solution was then washed twice with 50 ml of octane each time. The octane was decanted off, leaving 383.7 g of a methyl alcohol solution of 45% para-isopropylbenzyl triphenylphosphonium chloride in methanol.

Thereafter, 190 g of the above methyl alcohol/phosphonium chloride solution was placed into a flask, and the flask was additionally charged with 43.2 g of a 25% sodium methoxide in methanol solution at 8°–10° C., then 31.62 g of methoxycitronellal, also at 10°–13°C. Then after allowing the solution to sit for approximately 15 minutes, it was warmed to room temperature (i.e., approximately 22° C.) and thereafter heated to reflux temperature. The solution was refluxed for approximately 4 hours, then the heat was turned off and the reactants cooled to room temperature. Approximately 2 hours later the reactants were charged with 1 g of hydrogen peroxide and the solution was agitated. Another two hours later, the reaction solution was charged with 167.9 g of hexane and 100 ml of water, and agitation again commenced. Approximately 1.5 hours later the agitation was stopped, and the components allowed to separate into two phases.

There was obtained 277.6 g of an aqueous phase, and 233.6 g of an organic phase. The organic phase was washed twice with 75 g of methyl alcohol plus 30.1 g of water. The aqueous phase was decanted, yielding 221.4 g of organic material. This material was stripped at 90° C. under full vacuum and a nitrogen purge for 1.5 hours. There was obtained 47.5 g of 8-methoxy-4,8-dimethyl-1-(4-isopropylphenyl)-1-nonene, also known as dehydro-MV-678.

It will be appreciated by those skilled in the art that various changes can be made in the ratios of compounds used, temperatures and times without departing from the spirit and scope of the appended claims.

What is claimed is:

1. A process for the preparation of 8-methoxy-4,8-dimethyl-1-(4-isopropylphenyl)-nonene which comprises the steps of
   (a) reacting para-isopropylbenzyl chloride with triphenylphosphine in the presence of a methanol solvent for sufficient period of time and at a sufficient temperature to form an intermediate product in solution with methanol, para-isopropylbenzyl triphenylphosphonium chloride, and
   (b) reacting said methanol solution with sodium methoxide, followed by methoxycitronellal to produce 8-methoxy-4,8-dimethyl-1-(4-isopropylphenyl)-1-nonene, and
   (c) separating said intermediate product from the residual reactants.

2. The method of claim 1 in which step (a) of said reaction is conducted at a temperature of approximately 67° C.

3. The method of claim 1 in which there is used approximately 200 milliliters of methanol for every 0.25 gram/mole of active ingredient.

4. The method of claim 1 in which said intermediate product is separated from said residual reactants by adding hydrogen peroxide to the reaction mixture and hexane to extract the intermediate product.

5. The method of claim 1 which includes the further step of hydrogenating the intermediate product in the presence of ethanol or hexane and a palladium carbon catalyst to form 8-methoxy-4,8-dimethyl-1-(4-isopropylphenyl)-nonane.

6. A process for the preparation of 8-methoxy-4,8-dimethyl-1-(4-isopropylphenyl)-nonane which comprises the steps of:
   (a) reacting para-isopropylbenzyl chloride with triphenylphosphine in the presence of a suitable solvent at a temperature of and for a sufficient period of time to form a slurry of para-isopropylbenzyl triphenylphosphonium chloride in the solvent,
   (b) extracting the solids thus formed with methanol for a period of time sufficient to achieve phase separation between the solvent and methanol in which the para-isopropylbenzyl triphenylphosphoniuim chloride is then taken up in the methanol,
   (c) reacting said para-isopropylbenzyl triphenylphosphonium chloride solution with sodiuim methoxide, followed by methoxycitronellal at a temperature of and for a sufficient period of time to produce cis- and trans-8-methoxy-4,8-dimethyl-1-(4-isopropylphenyl)-1-nonene, and
   (d) hydrogenating said cis- and trans-8-methoxy-4,8-dimethyl-1-(4-isopropylphenyl)-1-none in the presence of a suitable solvent and a palladium carbon catalyst at a temperature of and for a sufficient period of time to produce the end product, 8-methoxy-4,8-dimethyl-1-(4-isopropylphenyl)-nonane.

7. The method of claim 6 in which step (a) is conducted in the presence of an n-octane solvent.

8. The method of claim 6 in which step (a) is conducted in the presenc of an n-heptane solvent.

9. The method of claim 6 in which step (a) is conducted at a temperature of about 100° C. for a period of time of about 25 hours.

10. The method of claim 6 in which step (a) is conducted at a temperature of about 135° C. for a period of about 6 hours.

11. The method of claim 6 in which the reactants of step (a) are present in a 84.6 to 111.5 to 102.8 weight ratio.

12. The method of claim 7 in which the reaction mixture of claim 1 is washed with hydrogen peroxide, followed by extraction by hexane, followed by washing with methanol and water, to remove triphenylhosphine oxide.

13. The method of claim 6 in which step (d) is conducted in the presence of a hexane solvent and the catalyst used is a palladiium-carbon combination.

* * * * *

UNITED STATES PATENT AND TRADEMARK OFFICE
CERTIFICATE OF CORRECTION

PATENT NO. : 4,482,751

DATED : November 13, 1984

INVENTOR(S) : Kambiz Javdani et al.

It is certified that error appears in the above-identified patent and that said Letters Patent is hereby corrected as shown below:

In Column 6, Claim 8, second line, the word "presenc" should read --- presence ---.

In Column 6, Claim 12, line 63, the word "triphenylhosphine" should read --- triphenylphosphine ---.

Signed and Sealed this

Twenty-first Day of January 1986

[SEAL]

Attest:

DONALD J. QUIGG

Attesting Officer

Commissioner of Patents and Trademarks